US012673223B2

(12) United States Patent
Winder et al.

(10) Patent No.: US 12,673,223 B2
(45) Date of Patent: Jul. 7, 2026

(54) ULTRASOUND STIMULATION OF MUSCULO-SKELETAL TISSUE STRUCTURES

(71) Applicant: Sonogen Medical, Inc, Chevy Chase, MD (US)

(72) Inventors: Alan Winder, Chevy Chase, MD (US); Robert Muratore, Chevy Chase, MD (US)

(73) Assignee: SONOGEN MEDICAL, INC., Chevy Chase, MD (US)

( * ) Notice: Subject to any disclaimer, the term of this patent is extended or adjusted under 35 U.S.C. 154(b) by 488 days.

(21) Appl. No.: 17/425,725

(22) PCT Filed: Jan. 24, 2020

(86) PCT No.: PCT/US2020/015009
§ 371 (c)(1),
(2) Date: Jul. 25, 2021

(87) PCT Pub. No.: WO2020/154633
PCT Pub. Date: Jul. 30, 2020

(65) Prior Publication Data
US 2022/0184424 A1      Jun. 16, 2022

Related U.S. Application Data

(60) Provisional application No. 62/797,009, filed on Jan. 25, 2019.

(51) Int. Cl.
*A61N 7/00*          (2006.01)
(52) U.S. Cl.
CPC ........ *A61N 7/00* (2013.01); *A61N 2007/0013* (2013.01); *A61N 2007/0073* (2013.01); *A61N 2007/0095* (2013.01)

(58) Field of Classification Search
CPC .............. A61N 7/00; A61N 2007/0013; A61N 2007/0073; A61N 2007/0095; A61N 2007/0039; A61B 8/085; A61B 8/00
See application file for complete search history.

(56) References Cited

U.S. PATENT DOCUMENTS

| | | | | | |
|---|---|---|---|---|---|
| 4,530,360 A | * | 7/1985 | Duarte | ............... | A61H 23/0245 607/51 |
| 5,520,612 A | * | 5/1996 | Winder | .................... | A61N 7/00 607/51 |

(Continued)

FOREIGN PATENT DOCUMENTS

| | | |
|---|---|---|
| EP | 0802770 B1 | 12/2000 |
| EP | 0843573 A1 * | 10/2003 |

(Continued)

OTHER PUBLICATIONS

Elegbe EC, Menon MG, McAleavey SA. Comparison of two methods for the generation of spatially modulated ultrasound radiation force. IEEE Trans Ultrason Ferroelectr Freq Control. Jul. 2011;58(7):1344-54. doi: 10.1109/TUFFC.2011.1954. PMID: 21768019; PMCID: PMC3403838. (Year: 2011).*

(Continued)

*Primary Examiner* — Pascal M Bui Pho
*Assistant Examiner* — Nicholas A Robinson
(74) *Attorney, Agent, or Firm* — F. CHAU & ASSOCIATES, LLC

(57)          ABSTRACT

A method for ultrasound stimulation of musculo-skeletal tissue structures includes generating a plurality of acoustic spatial-temporal modes comprised of a sinusoidal-complex, wherein the sinusoidal-complex has a modulation envelope that enhances spatial-temporal measurement accuracy at a site of a multi-layered biological tissue structure, and a pulse repetition frequency and duty cycle that are osteogenic at the site of the multi-layered biological tissue structure, beam (Continued)

steering the acoustic spatial-temporal modes to the site of the multi-layered biological tissue structure to promote tissue healing, and producing bi-modal stress levels in the multi-layered biological tissue structure that are sufficient to generate bone fracture healing.

7 Claims, 3 Drawing Sheets

(56) References Cited

U.S. PATENT DOCUMENTS

| | | | | |
|---|---|---|---|---|
| 5,752,924 | A | * | 5/1998 | Kaufman ................. A61N 7/00 601/2 |
| 6,446,509 | B1 | * | 9/2002 | Takada ................. G01N 29/245 73/598 |
| 7,410,469 | B1 | * | 8/2008 | Talish ...................... A61N 7/00 600/15 |
| 8,465,427 | B1 | * | 6/2013 | Qin ...................... A61B 8/0875 601/2 |
| 2004/0171970 | A1 | * | 9/2004 | Schleuniger .............. A61F 7/02 601/3 |
| 2006/0106424 | A1 | * | 5/2006 | Bachem ................... A61N 7/00 607/1 |
| 2007/0249969 | A1 | * | 10/2007 | Shields .................... A61N 7/00 601/2 |
| 2009/0131837 | A1 | * | 5/2009 | Granville ................. A61N 7/00 601/2 |
| 2009/0306551 | A1 | | 12/2009 | De Ana et al. |
| 2011/0196265 | A1 | | 8/2011 | Chang et al. |
| 2015/0231417 | A1 | * | 8/2015 | Metcalf ................... A61N 7/02 601/3 |
| 2019/0030374 | A1 | * | 1/2019 | Carpentier .............. A61N 7/00 |

FOREIGN PATENT DOCUMENTS

| | | | | | |
|---|---|---|---|---|---|
| EP | 0843573 | B1 | | 12/2003 | |
| EP | 1414521 | A1 | * | 10/2005 | |
| EP | 1414521 | B1 | | 10/2005 | |
| EP | 1180057 | B1 | | 8/2010 | |
| JP | 1998509605 | A2 | | 9/1998 | |
| JP | 2004537383 | A2 | | 12/2004 | |
| JP | 2008538714 | | | 11/2008 | |
| WO | WO 96/12519 | | | 6/1996 | |
| WO | WO 03/013654 | | | 2/2003 | |
| WO | WO-03013654 | A1 | * | 2/2003 | ............... A61N 7/00 |
| WO | WO 2005/071437 | | | 8/2005 | |
| WO | WO-2005071437 | A1 | * | 8/2005 | ......... G01S 15/8952 |
| WO | WO 2016/097867 | | | 6/2016 | |

OTHER PUBLICATIONS

S. Marvel, S. Okrasinski, S. H. Bernacki, E. Loboa and P. A. Dayton, "Applications of low intensity pulsed ultrasound for functional bone tissue engineering using adult stem cells," 2009 IEEE International Ultrasonics Symposium, Rome, Italy, 2009, (Year: 2009).*

A. Cafarelli, et al., "Speed of Sound in Rubber-Based Materials for Ultrasonic Phantoms," J Ultrasound. Dec. 2016; 19(4): 251-256. Published online Apr. 21, 2016.

Etana C. Elegbe, et al. "Comparison of Two Methods for the Generation of Spatially Modulated Ultrasound Radiation Force," IEEE Transactions on Ultrasonics, Ferroelectrics, and Frequency Control ( vol. 68, Issue: 7, Jul. 2011); pp. 1344-1354.

Supplementary Partial European Search Report dated Jan. 24, 2023, in corresponding European Patent Application 20745975, 5 pages.

Harrison, et al., "Mode & mechanism of low intensity pulsed ultrasounds (LIPUS) in fracture repair", available on the internet at http://dx.doi.org/10.1016/j.ultras.2016.03.016, Apr. 9, 2016, 9 pages.

Office Action in corresponding Japanese Patent Application No. 2021-543297, dated Jun. 4, 2024, 4 pages.

Israeli Office Action dated May 6, 2024, in corresponding Israeli Patent Application 285069, 3 pages.

* cited by examiner

ACOUSTIC MULTI-MODAL TESTING OF RABBIT FIBULA

ACOUSTIC MULTI-MODAL TESTING OF RABBIT FIBULA. CA1

ACOUSTIC MULTI-MODAL TESTING OF RABBIT FIBULA. CA2

RESULTS OF ANALYSIS $\theta$ = 31.5 degrees $\varphi$ = 63.0 degrees $\alpha$ = 73.5 ~ 88.2 degrees

ULTRASOUND STIMULATION OF MUSCULO-SKELETAL TISSUE STRUCTURES

CROSS-REFERENCE TO RELATED APPLICATION

This application is a National Phase of PCT application PCT/US20/15009, filed on Jan. 20, 2020, in the U.S. Receiving Office, which claims priority from U.S. Provisional Application No. 62/797,009, filed on Jan. 25, 2019 in the U.S. Patent and Trademark Office, the contents of which are herein incorporated by reference in their entirety.

BACKGROUND

Technical Field

Embodiments of the disclosure are directed to a multi-modal acoustic spatial-temporal signal with specific properties for dynamically generating the stimulation and characterization of deep biological tissue structures at frequencies that can efficiently invoke a cascade of cellular functions to accelerate tissue healing.

Discussion of the Related Art

The use of ultrasound to therapeutically treat and evaluate tissue and bone injuries is known. Impinging ultrasonic pulses having appropriate parameters, e.g., frequency, pulse repetition, and amplitude, for suitable periods of time and at a proper external location adjacent to the tissue or bone injury, have been determined to accelerate the natural healing of, for example, tissue tears, bone breaks and fractures.

Ultrasound wave propagation in tissue exerts a unidirectional radiation force on all absorbing and reflecting obstacles in its path, even at the microstructural level. The components of acoustic energy that can affect chemical change can be thermal, mechanical (agitational) and cavitational in nature. The largest non-thermal effects are those attributed to stable cavitation and mass transfer. These, in turn, can induce acoustic microstreaming, producing shear stresses on the cellular wall and boundary layer, and on the cytoskeleton. The latter effect, due to intracellular microstreaming, can produce an increase in the metabolic functions of the cell.

Since the early 1960s, the specific physical and biological mechanisms behind the therapeutic effectiveness of low intensity ultrasound have been extensively investigated. Low-intensity ultrasound refers to those power levels that just exceed biological thresholds which can trigger or evoke general biological regulatory reactions [1]. For spatial average-temporal average (SATA) intensities in the 0.1-0.5 $W/cm^2$ range, it is possible to produce non-thermal, high stress mechanisms of acoustic streaming and cavitation. In vitro tests on isolated fibroblast cells have shown that the effects of ultrasound on the cells are pressure sensitive, suggesting a (stable) cavitation mechanism [2,3], caused by the rapid expansion and collapse of microbubbles. The resulting bubble oscillations, possibly inducing acoustic microstreaming, can generate high shear stress on the cell membrane, which can affect the cell's permeability to sodium and calcium ions [4]. The increase in cell permeability may result in an increase in calcium uptake [5], an increase in protein and DNA synthesis in fibroblasts, and may account for the observed activation of macrophages. The production of fibroblasts and macrophages characterizes the normal fracture repair process. Hill [6] determined that the cavitation threshold is 0.1 $W/cm^2$ in an aqueous medium and ter Haar [7] estimated 0.2 $W/cm^2$ in vivo.

Low intensity ultrasound has been clinically demonstrated to enhance the process of angiogenesis or to increase blood flow around the bone fracture site, thereby further accelerating the healing of superficial musculoskeletal tissue wounds and bone fractures. Research studies have shown that there may exist a set of one or more acoustic signal excitations that maximally promote fracture healing by reducing the healing time and/or enhancing the quality of the regenerated tissue.

U.S. Pat. No. 4,530,360 to Duarte describes a basic non-invasive therapeutic technique and apparatus for applying ultrasonic pulses externally to the skin surface at a location adjacent to the bone injury. To apply the ultrasound pulses during treatment, an operator must manually hold the applicator in place until the treatment is complete. The Duarte patent as well as U.S. Pat. No. 5,520,612 to Winder, et al., describe ranges of RF signal for creating the longitudinal ultrasound waves, ultrasound power density levels, ranges of duration for each ultrasonic pulse, and ranges of ultrasonic pulse frequencies.

U.S. Pat. No. 6,213,958 B1 to Winder describes a diagnostic system to detect, localize, and characterize the acoustic emissions produced by applying noninvasive mechanical stimulation to the musculoskeletal system. Although the mechanical stimulation can either be static or dynamic, the Instron testing machine shown in FIG. 1 of the referenced patent implies that the excitation loading is static. The Winder invention would more readily facilitate clinical operation if the static loading could be replaced with external dynamic means.

U.S. Pat. No. 7,429,248 B1 to Winder, et al., describes a method and apparatus for controlling acoustic modes in tissue healing applications. The patent gives the same ranges of RF signal for creating the longitudinal ultrasound waves, ultrasound power density levels, ranges of duration for each ultrasonic pulse, and ranges of ultrasonic pulse frequencies as given in U.S. Pat. No. 5,520,612.

SUMMARY

Exemplary embodiments of the present disclosure are directed to a system and method of using an ultrasonic transducer/transmitter system to generate acoustic spatial-temporal modes that propagate to the site of a multi-layered biological tissue structure to promote tissue healing. These specific acoustic modes, produced by beam steering and characterized by their pulse repetition frequency, duty cycle, and bi-modal stress (intensity spatial-average temporal-average; $I_{SATA}$) levels, can significantly enhance bone fracture healing.

According to an embodiment of the disclosure, there is provided a method for ultrasound stimulation of musculo-skeletal tissue structures, including generating a plurality of acoustic spatial-temporal modes comprised of a sinusoidal-complex, wherein the sinusoidal-complex has a modulation envelope with structural details such that it enhances spatial-temporal measurement accuracy at a site of a multi-layered biological tissue structure, and a pulse repetition frequency and duty cycle that are osteogenic at the site of the multi-layered biological tissue structure, beam steering the acoustic spatial-temporal modes to the site of the multi-layered biological tissue structure to promote tissue healing, and producing bi-modal stress levels in the multi-layered biological tissue structure that are sufficient to generate bone fracture healing.

According to a further embodiment of the disclosure, the acoustic spatial-temporal modes include shear waves that promote integrin response of bone tissue extracellular matrix.

According to a further embodiment of the disclosure, the beam steering utilizes multi-element linear or planar phased arrays or a single element that drives a wedge block.

According to a further embodiment of the disclosure, when an angle of the acoustic spatial-temporal modes at a tissue layer boundary in the multi-layered biological tissue structure is less than a first critical angle, shear waves propagate along a fracture channel and longitudinal waves propagate at 30-60° with respect to the tissue layer boundary below a periosteal surface of bone tissue.

According to a further embodiment of the disclosure, when an angle of the acoustic spatial-temporal modes at a tissue layer boundary in the multi-layered biological tissue structure is substantially equal to the first critical angle, a combination of shear waves propagate along the fracture channel and longitudinal waves propagate at 60-90° with respect to the tissue layer boundary below and parallel to the periosteal surface of bone tissue.

According to a further embodiment of the disclosure, an angle of the acoustic spatial-temporal modes at a tissue layer boundary in the multi-layered biological tissue structure is substantially equal to a second critical angle, only shear waves propagate along and just below the periosteal surface of bone tissue.

According to a further embodiment of the disclosure, an acoustic intensity stress level per beam ranges from 30 to 70 milliwatts/cm$^2$ I$_{SATA}$.

According to a further embodiment of the disclosure, the acoustic intensity stress level per beam ranges from 40 to 50 milliwatts/cm$^2$ I$_{SATA}$.

According to a further embodiment of the disclosure, low frequencies of the acoustic spatial-temporal modes are osteogenic.

According to a further embodiment of the disclosure, the low frequencies range from 300 kHz to 3.0 MHz.

According to a further embodiment of the disclosure, the low frequency for long bone healing is 1.0 MHz.

According to a further embodiment of the disclosure, the low frequency for healing of cervical and lumbar fusions is 0.5 MHz.

According to a further embodiment of the disclosure, the modulation envelope is constant.

According to a further embodiment of the disclosure, the modulation envelope is a Gaussian function.

According to a further embodiment of the disclosure, low frequencies of the modulation envelope are produced by amplitude-modulation techniques wherein the sinusoidal-complex is represented as:

$$s(t)_{AM} = (1 + m \sin \omega_m t) \sin \omega_c t =$$
$$\sin \omega_c t - (m/2) \cos(\omega_c + \omega_m)t + (m/2) \cos(\omega_c - \omega_m)$$

wherein $\omega_c$ is the carrier frequency, m is a modulation index that controls a degree of amplitude modulation and $\omega_m$ is a modulation frequency.

According to a further embodiment of the disclosure, a lower sideband of the sinusoidal-complex utilizes 500 kHz- 1.0 MHz for bone tissue osteogenic repair and the upper sideband of the sinusoidal-complex utilizes 2.0-2.5 MHz for bone tissue imaging.

According to a further embodiment of the disclosure, the pulse repetition frequency (PRF) is equal to or less than 10 KHz.

According to a further embodiment of the disclosure, the pulse repetition frequency is about 1 kHz.

According to a further embodiment of the disclosure, the duty cycle ranges from 10-50%.

According to a further embodiment of the disclosure, the duty cycle is about 20%.

According to another embodiment of the disclosure, there is provided an ultrasonic transducer/transmitter system that includes a source of acoustic spatial-temporal modes comprised of a sinusoidal-complex that propagates to a site of a multi-layered biological tissue structure to promote tissue healing, wherein the source comprises a single transducer combined with a wedge block, or a multi-element linear or planar phased array that beam steers the acoustic spatial-temporal modes.

According to a further embodiment of the disclosure, the wedge block is composed of low viscous loss materials that include thermoplastics, thermosets, elastomers, or mixtures thereof.

According to a further embodiment of the disclosure, the wedge block has an acoustic impedance of 1.6+/−6% MRayls, is nontoxic in humans, and impermeable to human blood.

DETAILED DESCRIPTION OF EXEMPLARY EMBODIMENTS

Figure 1:
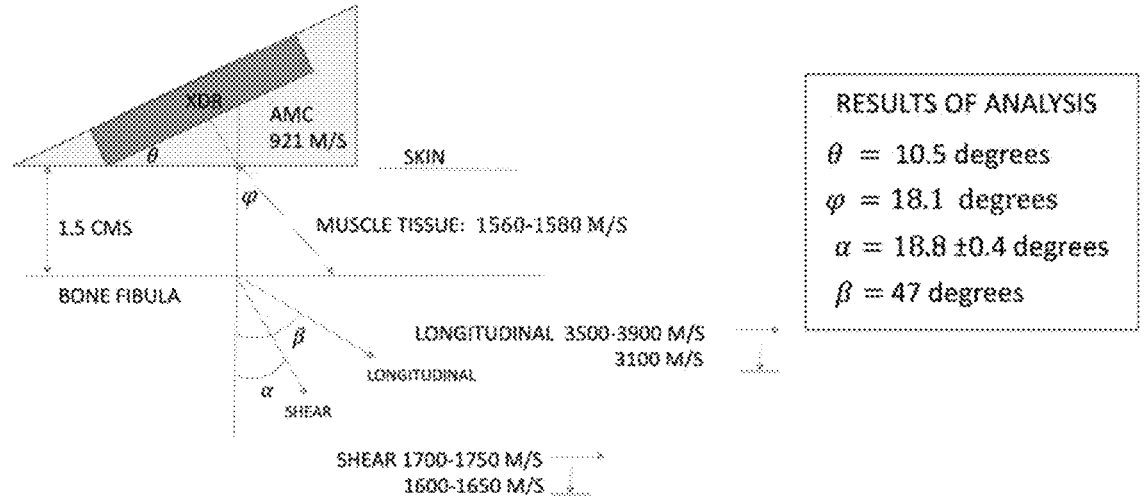
FIG. 1 illustrates the multi-modal transmission of an oblique NEWSIG into rabbit tissue for a beam-steering angle of 10.5 of the transducer face relative to the skin surface, according to embodiments of the disclosure.

Exemplary embodiments of the disclosure as described herein generally provide a method for generating a multi-modal acoustic signal at certain stress levels and frequencies that stimulates and characterizes deep biological tissue structures at frequencies that can accelerate tissue healing. While embodiments are susceptible to various modifications and alternative forms, specific embodiments thereof are shown by way of example in the drawings and will herein be described in detail. It should be understood, however, that there is no intent to limit the disclosure to the particular forms disclosed, but on the contrary, the disclosure is to cover all modifications, equivalents, and alternatives falling within the spirit and scope of the disclosure.

Embodiments of the disclosure are directed to the design and generation of a new multi-modal signal, rich in shear waves, to optimize the integrin response for the low frequency stimulation of biological tissue structures. This would be highly beneficial to both bone and wound healing, as well as (potentially) spinal fusion healing. Biomechanical principles are applied to the therapeutic treatment of fractures of the extremities, and metric measures are proposed to characterize the healing process. Embodiments of the disclosure provide radiation pressure and measured target response properties for, but not limited to, acoustic emission monitoring, bone tissue growth, bone fracture healing, spinal lumbar and cervical fusion, muscle reeducation, and tissue wound healing.

The exogenous use of acoustic waves to efficiently enhance the diagnosis, therapy, and surgery of a biological system depends on a detailed understanding of the system's physical properties, such as particle displacement, particle velocity, stress, strain, and elasticity. In particular, if stimulated properly, bone tissue can support remodeling and remineralization in the final healing phase.

LIPUS Stimulation Produces a Bone Healing Physiological Response

Animal connective tissues consist largely of an extracellular matrix comprised mainly of collagen, the chief protein in bone that cells secrete around themselves. It is the collagen in this matrix that gives supportive tissues their tensile strength. Low-intensity pulsed ultrasound (LIPUS) stimulation of the extracellular matrix outside a cell is transferred across a weak plasma membrane to the cytoskeleton in an animal cell via molecular protein linkages called integrins. Research has shown that ultrasonic waves enhance the cellular integrin response that initiates a cascade of intracellular pathway events. These events include: (1) increasing the permeability of the cellular wall membrane of the extra-cellular matrix; (2) affecting certain cytoplasm growth factors, such as TGF-β, PDGF, EGF, (a, b)FGF, IGF-I,II, and NGF, that produce a transcription of specific genes; and (3) utilizing mRNA to translate specific gene transcriptions to the nucleus to activate protein synthesis. Specifically, research has also shown that LIPUS enhances soft callus mineralization (endochondral ossification) in the second stage of healing and further increases the fracture hard callus strength in the remineralization and remodeling phases that occur in the third (and last) stage of healing.

Therefore, the integrin molecular protein response is key to generating the cellular function of protein synthesis, resulting in a clinical bone healing physiological response. In vitro experiments have shown that integrins respond best to shear wave radiation pressure. Thus, a signal that stimulates bone tissue repair should be rich in shear waves and be matched to the biological response relaxation times of bone tissue. This will maximize the callus index, defined as the ratio of the callus diameter to bone diameter, and the bone density in the fracture channel.

Shear Wave Generation

According to an embodiment of the disclosure, shear waves can be generated by a specially designed coupling wedge serving as an acoustic modal converter (AMC) that can spatially control the acoustic longitudinal waves transmitted normal to the bone by a piezoelectric transducer to produce both shear and longitudinal waves interior to the bone surface. This is explained in more detail below.

The particle direction of shear waves is normal to the propagation direction, permitting two types of shear waves to exist, namely, shear horizontal (SH) and shear vertical (SV), depending upon the direction of particle oscillation with respect to the propagation direction. In general, a random shear wave incident at a boundary between two different solid media contains both SH and SV components. Furthermore, SV waves can undergo modal conversion according to the boundary condition established by Snell's Law that also governs the interaction of the longitudinal wave at the interface between a medium 1 and a medium 2:

$$(\sin \theta_s/C_s)_1 = (\sin \theta_L/C_L)_1 = (\sin \theta_L/C_L)_2 = (\sin \theta_s/C_s)_2, \quad (1)$$

where $\theta_s$ is the shear angle, $\theta_L$ is the longitudinal angle, $C_s$ is the shear velocity, and $C_L$ is the longitudinal velocity. Note that the shear angle and the longitudinal angle are measured for, respectively, the shear velocity and longitudinal velocity with respect to a normal to the bone tissue. In contrast, SH waves cannot undergo modal conversion. Instead, SH waves maintain motion relative to the boundary. An acoustic waveguide, such as a bone fracture channel, can support pure SH waves.

EQ. (1) demonstrates that when a wave moves from a slower to a faster material, there is an incident angle, known as the first critical angle, which makes the angle of refraction for the longitudinal wave 90 degrees. If the angle of incidence becomes greater than the first critical angle, only the shear wave propagates into the material. In most materials, there is also an incident angle that makes the angle of refraction for the shear wave 90 degrees. This is referred to as the second critical angle.

Embodiments of the disclosure can optimize the longitudinal and shear content of interacting acoustic waves to enhance a bone healing physiological response, and promote integrin response of bone tissue extracellular matrix.

Acoustic Modal Converter Design and Construction

Beam steering can control the relative amount of propagating longitudinal and shear energy in bone tissue, and the amount of heat energy generated. The control of beam steering angles is known in underwater sonar, radar, and medical applications, and is achieved in several different ways utilizing: (1) multi-element linear or planar phased arrays of transducer elements; and (2) single transducers embedded in intermediate wedges of various materials that control the relative indices of refraction between transducer/wedge and intervening biological material layers. Signal steering is done by adjusting the relative phase (timing) of the waveform emitted by each element, which effectively cancels the wave propagation in one or more directions and reinforces it in other directions. Linear arrays are arrays of rectangular transducer elements which by their shape produce a non-hemispherical propagating wave. The elements of a linear array can also be phased to further steer the beam.

According to an embodiment, a specially designed coupling wedge acting as an acoustic modal converter (AMC) is a simple approach in medical ultrasound research to producing both normal and oblique longitudinal modes to be propagated to the bone fracture. The coupling wedge is generally considered to be a viscoelastic material. An AMC according to an embodiment includes suitable low viscous loss materials that include, but are not limited to, thermoplastics, thermosets, elastomers, or mixtures thereof. AMC design considerations include the velocity of sound, acoustic attenuation, acoustic impedance, toxicity in humans, permeability to human blood, and ability to produce an acoustic free-field from the embedded radiating transducer. An AMC according to an embodiment has an acoustic impedance of 1.6+/−6% MRayls, is nontoxic in humans, and impermeable to human blood.

Biological System Model

According to an embodiment of the disclosure, to determine a balance between shear and longitudinal modes, an insonified structure is modeled as a parallel four-layer system, where the outermost three layers (skin, fat and muscle) behave as viscous fluids and the innermost fourth layer (bone) behaves as a viscoelastic solid. Bone tissue should be characterized with both viscous and elastic components to meaningfully affect bone fracture repair.

According to an embodiment, a propagating longitudinal acoustic signal that is incident on a tissue layer boundary at an oblique angle has three components: (1) a reflected longitudinal signal where the reflection angle equals the incident angle; and a bi-modal signal transmitted into the interior of the bone, propagating as both (2) shear and (3) longitudinal waves. The bi-modal signal incident at the muscle/bone tissue interface, rich in both longitudinal and shear wave content, is referred to herein below as a new acoustic signal ("NEWSIG").

According to an embodiment, the effectiveness of the NEWSIG depends on providing sufficient energy to the acoustic modes, matched to the unique character of each mode, that is, whether it is longitudinal or shear. However, shear waves are more lossy than longitudinal waves, and to utilize them, their intensity levels should be increased relative to that of the longitudinal waves.

According to an embodiment, the increase in shear intensity in bone tissue is based on empirical research studies. The longitudinal attenuation coefficient, $\alpha_L$, for acoustic waves at normal incidence to the bone in the low therapeutic frequency band of 1-4 MHz, is:

$$\alpha_L = 4.2 \ dB/MHz\text{-}cm. \tag{2}$$

The shear attenuation coefficient, as, for generating acoustic shear waves via the mode conversion method, is:

$$\alpha_s = 7.0 \ dB/MHz\text{-}cm. \tag{3}$$

Therefore, according to an embodiment, for multi-mode excitation, the intensity spatial-average temporal-average ($I_{SATA}$) for the longitudinal modal component should be about 0.6 the $I_{SATA}$ for the accompanying shear mode. Thus, if the $I_{SATA}$ for longitudinal excitation is about 30 mW/cm², then the $I_{SATA}$ for shear excitation should be about 50 mW/cm².

According to an embodiment, adjusting the intensity can produce an effective shear mode for multi-modal tissue healing. These adjustments compensate for the fact that the shear waves travel slower than longitudinal waves and dissipate more heat energy in propagating through bone tissue.

New Signal Acoustic Stimulation

According to an embodiment, the new signal, a NEWSIG can accelerate both the treatment of long bone fracture healing and promote the healing of lumbar and cervical spine fusions. A NEWSIG according to an embodiment has sufficient spectral energy in a specific range of low frequencies, such that there will be several biological osteogenic effects: (1) an increase in the permeability of the cellular wall membrane, which enhances the diffusion process for calcium uptake and protein synthesis; (2) an increase in the hemoglobin released; and (3) effect the gene expression within the insonated tissue.

Figure 4:
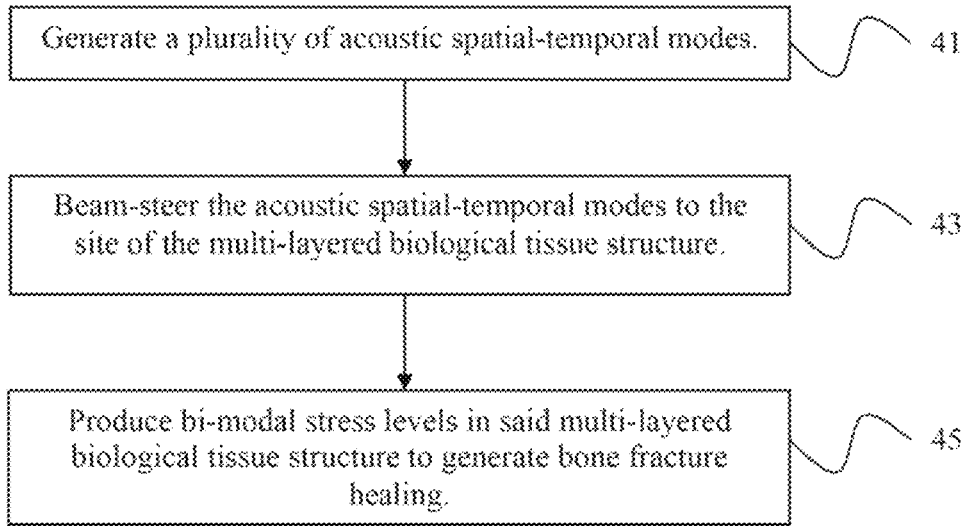
FIG. 4 is a flowchart of a method for ultrasound stimulation of musculo-skeletal tissue structures, according to an embodiment of the disclosure.

FIG. 4 is a flowchart of a method for ultrasound stimulation of musculo-skeletal tissue structures, according to an embodiment of the disclosure. Referring to the figure, the method begins at step 41 by generating a plurality of acoustic spatial-temporal modes. The acoustic spatial-temporal modes include a sinusoidal-complex that has a modulation envelope whose structural details enhance spatial-temporal measurement accuracy at a site of a multi-layered biological tissue structure, and a pulse repetition frequency and duty cycle that are osteogenic at the site of the multi-layered biological tissue structure. The acoustic spatial-temporal modes are beam-steered at step 43 to the site of the multi-layered biological tissue structure to promote tissue healing, and at step 45 produce bi-modal stress levels in said multi-layered biological tissue structure that are sufficient to generate bone fracture healing. The acoustic spatial-temporal modes include shear waves that promote integrin response of bone tissue extracellular matrix.

To date, the Duarte Signal is the only FDA-approved acoustic signature for accelerating the healing of long bone fractures. A Duarte signal has a nominal frequency of the ultrasound is 1.5 MHz, the width of each pulse varies between 10 and 2,000 microseconds, the pulse repetition rate varies between 100 and 1,000 Hz, and the power level of the ultrasound is maintained below 100 milliwatts per square centimeter. The primary difference between the Duarte Signal and a NEWSIG according to an embodiment is that the Duarte Signal is a higher frequency longitudinal wave while a NEWSIG is a lower frequency longitudinal+ shear wave that results in greater healing osteogenic action at deeper penetration of biological bone tissue.

New Signal Spectral Energy

The primary spectral energy content of a NEWSIG according to an embodiment lies in the frequency band from 3 Hz to 3 MHz, has a pulse repetition frequency (PRF) less than 10 kHz, a duty cycle from 10-50%, an $I_{SATA}$ from 3-400 mW/cm², a modulating envelope from constant to Gaussian and a dosage time less than 60 minutes.

According to an embodiment, a NEWSIG for musculo-skeletal bone healing of short and long bone fractures and for promoting spinal fusion has the following characteristics: spectral energy of 300 kHz to 3.0 MHz, a constant or Gaussian envelope, a maximum PRF of 1 kHz, a duty cycle≤20%, an $I_{SATA}$ from 30 to 150 mW/cm² at the skin interface, and a daily dosage time equal to or less than 20 minutes. Due to signal demodulation that occurs in the fracture channel, a PRF of 1 kHz is better matched to the relaxation time of bone tissue, in the low 1 millisecond region.

In an embodiment, the low frequencies of the acoustic spatial-temporal modes are osteogenic, and range from 300 kHz to 3.0 MHz. According to an embodiment, the low frequency for long bone healing is 1.0 MHz, and the low frequency for healing of cervical and lumbar fusions is 0.5 MHz. In some embodiments, an acoustic intensity stress level per beam ranges from 30 to 70 milliwatts/cm² $I_{SATA}$, and in other embodiments, the acoustic intensity stress level per beam ranges from 40 to 50 milliwatts/cm² $I_{SATA}$.

Amplitude Modulation Stimulation

According to an embodiment, an osteogenic spectral envelope can be obtained by utilizing well known amplitude and frequency modulation technology. The simplest amplitude modulation method utilizes the phased linear sum of transmitted sinusoidal waves in the focal zone, represented by the following trigonometric identity:

$$s(t)_{AM} = \sin A + \sin B = 2 \cos((A-B)/2)\sin(A+B)/2) = 2 \cos(\Delta t)\sin(w_c + \Delta)t \tag{4}$$

where s(t) is the transmitting signal, $A = B + 2\Delta \cdot t$; $B = \omega_c t$, $\omega_c$ is the carrier frequency and A is the desired low osteogenic frequency.

According to an embodiment, another low spectral frequency envelope is produced by varying the magnitude of the carrier in accordance with the amplitude and frequency of the modulating source. For a sinusoidal source, this can be represented as:

$$s(t)_{AM} = (1 + m \sin \omega_m t) \sin \omega_c t = \qquad (5)$$
$$\sin \omega_c t - (m/2) \cos(\omega_c + \omega_m)t + (m/2) \cos(\omega_c - \omega_m)t$$

where the signal spectrum can be characterized as the sum of the carrier with upper and lower sidebands; (m) is generally referred to as the modulation index and controls the degree of amplitude modulation and $\omega_m$ is the modulation frequency.

According to an embodiment, by suppressing the carrier, through judicious selection of the carrier frequency $\omega_c$ and modulation frequency $\omega_m$, osteogenic stimulation may be optimized. The spatial array directivity and range resolution increases with frequency, with the result that finer pathology details can be discerned in tissue images. According to an embodiment, the higher sideband of 2.0 to 2.5 MHz provides more spatial and range resolution and higher SNR for increased detectability and is therefore used for bone tissue diagnostic imaging, but is limited by the associated energy absorption that increases with increasing frequency, making it tissue-depth-limited. On the other hand, the lower sideband of 500 kHz to 1.0 MHz is primarily useful for bone tissue osteogenic repair at deeper depths, but is limited by cavitation effects that increase with decreasing frequency.

Proof-of-Concept (POC) Study

A randomized, double-blind POC study has shown that the clinical potential of a multi-modal transmission according to an embodiment is that such treatment initially enhances critical revascularization in the initial inflammatory phase and again at the end of the soft callus phase, just before bone tissue remodeling adapts to mechanical requirements in the final hard callus phase.

A POC study according to an embodiment was modeled after Pilla's work at Mt Sinai, N.Y.C., and depends on published research over the past forty years measuring the properties of shear waves in biological tissue.

Figure 2:
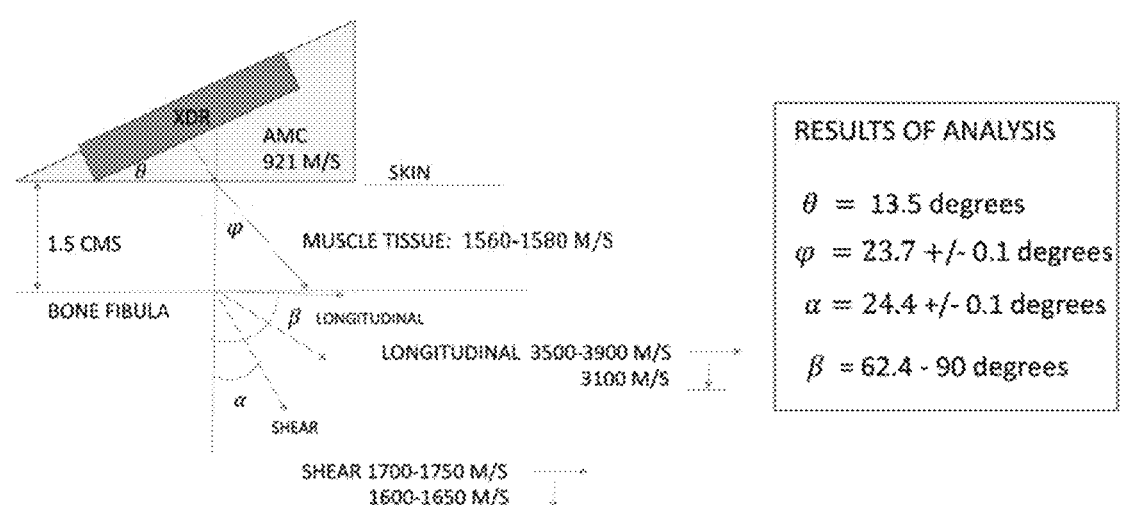
FIG. 2 illustrates the multi-modal transmission of an oblique NEWSIG into rabbit tissue for a beam-steering angle of 13.5° (the first critical angle (CA1)) of the transducer face relative to the skin surface, according to embodiments of the disclosure.
Figure 3:
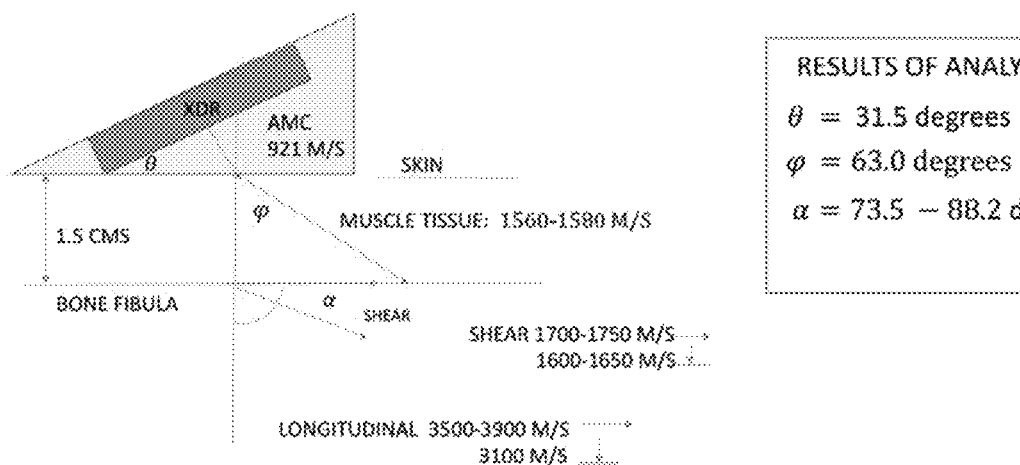
FIG. 3 illustrates the multi-modal transmission of an oblique NEWSIG into rabbit tissue for a beam-steering angle of 31.5° (the second critical angle (CA2)) of the transducer face relative to the skin surface, according to embodiments of the disclosure.

A POC study according to an embodiment used AMCs that produced an oblique NEWSIG at 10.5°, a NEWSIG at 13.5°, and a NEWSIG at 31.5°. These angles are oblique angles of the measured signal at the AMC/skin interface as shown in FIGS. 1-3, respectively. The AMCs were positioned to support systemic blood flow (from distal to proximal). The signal transmission power levels were adjusted to compensate for absorption through the AMC. The spatial average-temporal average intensity ($I_{SATA}$) at the wedge/skin interface was adjusted to be 30 mW/cm² for transmitted normal longitudinal waves and 40 mW/cm² for oblique longitudinal waves.

FIGS. 1-3 illustrate the multi-modal transmission of an oblique NEWSIG into rabbit tissue for various angles of the transducer face relative to the skin surface, according to embodiments of the disclosure. In the figures:

θ is the oblique angle of the transducer face relative to the skin surface, with 0° representing the transducer face parallel to the skin for normal transmission;

φ is the refracted angle of the ultrasound wave propagating from the AMC into the tissue, measured relative to the perpendicular (normal);

α is the refracted angle of the shear portion of the ultrasound wave propagating from the overlying tissue into the bone, measured relative to the perpendicular (normal);

β is the refracted angle of the longitudinal portion of the ultrasound wave propagating from the overlying tissue into the bone, measured relative to the perpendicular (normal); and the triangle is the acoustic wedge AMC, and XDR is the transducer.

The estimated thickness of the muscle tissue between the skin surface to the bone fibula is 1.5 cm, the measured longitudinal velocity of the acoustic wave for the AMC material is 921 m/s, and the phase velocity through the muscle tissue is from 1560 to 1580 m/s. Assuming the bone to extend in the x-axis and a fracture to extend along the y-axis, the phase velocity of the longitudinal components is 3500-3900 m/s along the surface of the bone tissue and 3100 m/s along the fracture channel, and the phase velocity of the shear components is 1700-1750 m/s along the surface of the bone tissue and 1600-1650 m/s along the fracture channel.

FIG. 1 illustrates a case for which θ=10.5°, for which φ=18.1°, α=18.8±0.4° and β=47°. FIG. 2 illustrates a case for which θ=13.5°, for which φ=23.7±0.1°, α=24.4±0.1° and β ranges from 62.4 to 90°. FIG. 3 illustrates a case for which θ=31.5°, for which φ=63° and α=ranges from 73.5 to 88.2°.

The POC study results shown in FIGS. 1-3 show that when an angle of the acoustic spatial-temporal modes at a tissue layer boundary in the multi-layered biological tissue structure is 10.5°, less than the first critical angle of 13.5°, comprised of shear waves that propagate along a fracture channel at about 19° and longitudinal waves that propagate at 30-60° with respect to the tissue layer boundary below a periosteal surface of bone tissue. In addition, when an angle of the acoustic spatial-temporal modes at a tissue layer boundary in the multi-layered biological tissue structure is substantially equal to the first critical angle, a combination of shear waves propagate along the fracture channel at about 24° and longitudinal waves propagate at 60-90° with respect to the tissue layer boundary below and parallel to the periosteal surface of bone tissue. Furthermore, when an angle of the acoustic spatial-temporal modes at a tissue layer boundary in the multi-layered biological tissue structure is substantially equal to 31.5°, which is the second critical angle, only shear waves propagate along and just below the periosteal surface of bone tissue.

POC torsional test results with 17 rabbits having surgically-induced bilateral fibular osteotomies showed that a test device, with NEWSIG excitation, was superior to the current FDA-approved device, with Duarte Signal excitation, after undergoing treatment for 18 days (POD 1 to POD 18; POD-post operative day) with euthanasia on POD 21. Statistical analysis showed that the maximum torque increased by 25.3% (p=0.0215) and stiffness increased by 25.7% (p=0.0501) relative to the Duarte signal. Of the two AMCs tested, the shear wave mode for 31.5° appeared to be superior for a bone growth stimulation (BGS) application.

Biological Medium Considerations

According to an embodiment, design of a BGS signal should consider the linear and nonlinear characteristics of the propagating medium. The dynamics of living tissue are generally nonlinear; however, to facilitate the understanding and visualization of physical phenomena, the response to various stimuli is linearized, both naturally-occurring in nature and man-made. This linearization process is well-known and is often termed the small-amplitude case. The small-amplitude or low intensity case is considered non-thermal and therefore produces biological effects through mechanical stimulation, only, which can be either static or dynamic.

The two most well-known non-thermal nonlinear effects are cavitation and acoustic streaming. Common measures of non-thermal nonlinear ultrasound behavior in biological tissue are the mechanical index (MI) and the beam nonuniformity ratio (BNR). A measure of the nonlinear thermal effects due to the acoustic power causing the tissue temperature to rise by 1° C. is referred to as the thermal index (TI).

The MI is a measure of the destructive behavior of ultrasound induced in biological tissue due to cavitation effects, and is intended for B-mode short-pulse, low duty cycle (<2%) diagnostic imaging where high peak pressures are often obtained.

The 1992 AIUM-NEMA Standard proposes an acceptable value for MI of less than 0.7 (p. 144, Section 7.1) in the unscanned mode, below which cavitation (theoretically) will not occur. It was assumed that stabilized pockets of gas or free bubbles exist in vivo—which clinically, other than for contrast agents, is still not certain. The tested FDA-approved device produces an MI<0.1 for 20 Vp-p and 1.5 MHz and the test device produces an MI<0.2 for 25 Vp-p and 1.0 MHz.

The BNR is defined as the [max ISPTA/$I_{SATA}$], where [max ISPTA] is at the acoustic axial distance of maximum pressure, which for unfocused transducers is at a point approximately the (transducer diameter)$^2$/(4×wavelength λ), and $I_{SATA}$ is the total acoustic power divided by the Effective Radiation Area (ERA). The ERA is the width of the beam intensity profile function at the −13 dB point, at a distance of 5 mm along the transducer axis; measured in the in vivo POC study referred to earlier to be about 130 mm. The ERA in the study is approximately equal to 3.88 cm$^2$, corresponding to an electrode diameter of 0.875 inches or 22.22 mm. The maximum measured value of BNR for the test device in the POC study was less than 5.0. The FDA requires that the BNR for therapeutic devices be less than 8.0 and that the measured maximum value be indicated on the label of the device.

For therapeutic applications of the musculo-skeletal system, the thermal index of importance for long bones, scaphoid, metatarsal and head depends on the bone near the surface and is designated the thermal index for cranial bone (TICB), $$TICB = W_o/40D_{eq}, \qquad (6)$$

where $W_o$ (in mW) is the time average acoustic power at the radiated surface of the transducer and $D_{eq}$ is the equivalent diameter (in cm) of the active (or electroded) transducer area.

Design Considerations of a Low Frequency Transducer Projector

According to an embodiment, the low osteogenic frequencies characterized by a NEWSIG can be generated by a transducer having electromagnetic, piezoelectric, electrostrictive, or magnetostrictive active elements. The active elements can be in the form of a single or multilayer component made of one or combination of materials named above. In addition, the active elements can be made of composites of such materials with polymeric, void and/or metallic components. Moreover, active elements made of such materials can generate low frequency waves via flextensional effects attainable with unimorphs, monomorphs, bimorphs, cymbals, moonies, thunders, rainbows, cerambows, etc, known by those skilled in the art. In addition, the frequencies mentioned in the embodiment can be generated by mechanical vibrations of air molecules or molecules of a medium in contact with human body using speakers, buzzers, tuning forks, and/or any nonactive mechanical vibrating elements being driven by the active elements mentioned above. Furthermore, the low osteogenic frequencies disclosed here can also be generated by transducers made of micro-electro-mechanical ultrasonic transducers (MUTs). Examples of such MUTs include a capacitive microelectromechanical ultrasonic transducer (CMUT) and a piezoelectric microelectromechanical ultrasonic transducer (PMUT). The CMUT and PMUT can be stand-alone transducers or be integrated on an electronic circuit board driving such MUTs.

Unique Features in this Disclosure

Embodiments of the disclosure provide at least five (5) unique features, namely:

1. Optimizing the acoustic spatial-temporal transmitted signal to enhance the integrin response of the bone tissue electro-cellular matrix.
2. Adjusting the $I_{SATA}$ intensity on transmit, the carrier and pulse repetition frequencies and the oblique longitudinal angle of the transmitted signal excitation are necessary to enhance both endosteal and periosteal healing at the bone fracture site.
3. Controlling the bone healing physiological response by the transmitted beam steering angle to produce the proper mix of longitudinal and shear waves in the fracture channel.
4. Producing the required oblique longitudinal signal through the use of multi-element linear or planar phased arrays, or by other means, such as acoustic modal converters using thermal plastic and elastic silicone rubber materials.
5. Positioning the beam steered transducer on the skin during treatment to support angiogenic systemic (oxygenated) blood flow.

From the foregoing, it will be appreciated by those skilled in the art that embodiments of the present disclosure provides an effective method and apparatus for overcoming many limitations associated with the mechanical stimulation of biological materials. It will also be readily appreciated by one with ordinary skill in the art to use the method and apparatus of embodiments of the present disclosure in other applications, such as in therapeutic ultrasound, as related to bone fracture and wound healing, for example.

Although certain exemplary embodiments of the present disclosure have been specifically described herein, it will be apparent to those skilled in the art to which the disclosure pertains that variations and modifications of the exemplary embodiments shown and described herein may be made without departing from the spirit and scope of this disclosure.

REFERENCES

1. Sarvazyan A P, *Some General Problems of Biological Action of Ultrasound*, IEEE Trans SU, 30 (1): 2-12, 1983.
2. Clarke P R and Hill C R, *Physical and Chemical Aspects of Ultrasonic Disruption of Cell*, JASA, 47 (2): 649-653, 1969.
3. Webster D F, Harvey W, Dyson M, Pond J B, *The Role of Ultrasound-Induced Cavitation in the 'In Vitro' Stimulation of Collagen Synthesis in Human Fibroblasts*, Ultrasonics: 33-37, 1980.

4. Dyson M, *Therapeutic Applications of Ultrasound*, In *Biological Effects of Ultrasound*, Nyborg W L and Ziskin M C, eds., Churchill Livingstone Inc, New York, 1985: Chapter 11.
5. Berridge M J, *Elementary and Global Aspects of Calcium Signalling*, Journal of Physiology, (1997), 499, 2:291-306.
6. Hill C R, *Ultrasonic Exposure Thresholds for Changes in Cells and Tissues*, JASA, 52 (2): 667-672, 1972.
7. Ter Haar G, Review of Therapeutic Ultrasound, European Journal of Ultrasound, 9, (1999): 3-9.

What is claimed is:

1. A method for ultrasound stimulation of musculo-skeletal tissue structures, the method comprising the steps of:

generating a sinusoidal-complex in an acoustic spatial-temporal shear mode, wherein the sinusoidal-complex in the acoustic spatial-temporal shear mode is represented as $$s(t)_{AM} = (1 + m \sin \omega_m t) \sin \omega_c t =$$
$$\sin \omega_c t - (m/2) \cos(\omega_c + \omega_m)t + (m/2) \cos(\omega_c - \omega_m)$$

t, wherein $s(t)_{AM}$ is a transmitting signal, t is time, $\omega_c$ is a carrier frequency, m is a modulation index that controls a degree of amplitude modulation, and $\omega_m$ is a modulation frequency; and beam-steering the sinusoidal-complex along a bone axis of a musculo-bone fracture tissue in a multi-layered biological tissue structure;

wherein the beam-steered sinusoidal complex in the acoustic spatial-temporal shear mode activates an integrin response of a bone tissue extracellular matrix through shear-wave stimulation;

wherein the beam-steered sinusoidal complex in the acoustic spatial-temporal shear mode produces an effective amount of shear stress levels in the multi-layered biological tissue structure that biophysically stimulates bone tissue repair and bone fracture healing in the musculo-bone fracture tissue, beginning with periosteal healing in the musculo-bone fracture tissue, wherein a transmitting signal amplitude modulation envelope of the sinusoidal-complex in the acoustic spatial-temporal shear mode is constant, an osteogenic acoustic intensity shear stress level per beam of the sinusoidal-complex in the acoustic spatial-temporal shear mode is 50 milliwatts/cm², a pulse repetition frequency (PRF) of the sinusoidal-complex in the acoustic spatial-temporal shear mode for bone tissue repair is 1 kilohertz (kHz), a duty cycle of the sinusoidal-complex in the acoustic spatial-temporal shear mode is about 20%, a frequency of the sinusoidal-complex in the acoustic spatial-temporal shear mode for long bone healing is 1.0 megahertz (MHz) and a frequency of the sinusoidal-complex in the acoustic spatial-temporal shear mode for spinal fusion healing is 0.5 megahertz MHz, and a dosage time of the sinusoidal-complex in the acoustic spatial-temporal shear mode is equal to or less than 20 minutes, and wherein the osteogenic acoustic intensity shear stress level, PRF, the duty cycle, the frequency for the long bone healing, the frequency for the spinal fusion healing, and the dosage time have been simultaneously optimized to produce the amount of the shear stress levels in the multi-layered biological tissue structure that biophysically stimulates the bone tissue repair and the bone fracture healing in the musculo-bone fracture tissue.

2. The method of claim 1, wherein the carrier frequency of the sinusoidal-complex that promotes the bone fracture healing is between 0.5 megahertz MHz and 1.5 MHz.

3. The method of claim 1, wherein 1/PRF is matched to a relaxation time of the stimulated bone tissue repair by the sinusoidal-complex.

4. The method of claim 1, wherein the sinusoidal-complex in the acoustic spatial-temporal shear mode is generated by an ultrasonic transducer or transmitter system that includes a power supply, a microcontroller, a signal generator, a beamformer, one or more power amplifiers, a single transducer or a phased array, and a display.

5. The method of claim 4, further comprising beam-steering the sinusoidal complex to the fracture site using the phased array.

6. The method of claim 4, further comprising beam-steering the sinusoidal-complex to the musculo-bone fracture tissue by the single transducer, wherein the single transducer is an acoustic modal converter (AMC) in a form of a wedge block, wherein the wedge block forms an angle that is substantially equal to or less than a second critical angle of the sinusoidal-complex, includes one or more of a thermoplastic, a thermoset, an elastomer, or a mixture thereof, is nontoxic in humans, and is impermeable to human blood.

7. The method of claim 6, wherein the wedge block has an attenuation of less than 7 decibel (dB) per centimeter at 1.5 MHz.

* * * * *